United States Patent

Katou et al.

[11] Patent Number: 5,965,448
[45] Date of Patent: Oct. 12, 1999

[54] PRECIPITATION SEPARATION TYPE CONTINUOUS FLOW ANALYTICAL APPARATUS AND QUANTITATIVE ANALYSIS OF THIOUREA IN COPPER ELECTROLYTE

[75] Inventors: Masaaki Katou; Yutaka Hayashibe; Minoru Takeya; Yasumasa Sayama, all of Omiya, Japan

[73] Assignee: Mitsubishi Materials Corporation, Tokyo, Japan

[21] Appl. No.: 08/943,412

[22] Filed: Sep. 30, 1997

[30] Foreign Application Priority Data

Sep. 30, 1996  [JP]  Japan ................................. 8-258400
Sep. 30, 1996  [JP]  Japan ................................. 8-258401

[51] Int. Cl.⁶ .......................... G01N 35/08; G01N 21/05
[52] U.S. Cl. .............................. 436/52; 436/111; 436/119; 436/164; 436/177; 422/63; 422/68.1; 422/81
[58] Field of Search .................. 436/52, 53, 111, 436/174, 175, 177, 119, 120; 422/63, 68.1, 81

[56] References Cited

U.S. PATENT DOCUMENTS

| | | | |
|---|---|---|---|
| 3,098,719 | 7/1963 | Skeggs | 436/177 |
| 4,520,108 | 5/1985 | Yoshida et al. | 436/53 |
| 4,582,687 | 4/1986 | Kuroishi et al. | 436/53 |
| 5,252,486 | 10/1993 | O'Lear et al. | 436/52 |
| 5,344,571 | 9/1994 | Mendershausen et al. | 210/723 |
| 5,387,524 | 2/1995 | Hayashibe et al. | 436/52 |
| 5,468,643 | 11/1995 | Su et al. | 436/161 |
| 5,624,846 | 4/1997 | Hayashibe et al. | 436/177 |
| 5,633,168 | 5/1997 | Glasscock et al. | 436/177 |

FOREIGN PATENT DOCUMENTS 407258879  10/1995  Japan.

OTHER PUBLICATIONS

Cyganski, A. "Determination of Some Organic Thio–Compounds by Precipitation of Mercuric Sulphide from Mercury(II) Ammine Complexes–II Determination of Thiourea and Some of its Derivatives." Talanta, 52–53, 1978.

Primary Examiner—Arlen Soderquist
Assistant Examiner—Kevin P. Cannell
Attorney, Agent, or Firm—Oblon, Spivak, McClelland, Maier & Neustadt, P.C.

[57] ABSTRACT

A flow injection analytical apparatus which is capable of continuously performing flow analysis of a sample, produces precipitates during the flow through a capillary. The precipitation separation type continuous flow analytical apparatus has a sample injection portion, a reagent addition portion and an analytical portion which are integrally communicated by a measurement pipeline to form a measurement system. A precipitant addition portion and a filtration portion are provided between the sample injection portion and the reagent addition portion in order to continuously perform production and filtration of precipitates during flow of the sample solution to the reagent addition portion.

8 Claims, 5 Drawing Sheets

PRECIPITATION SEPARATION TYPE CONTINUOUS FLOW ANALYTICAL APPARATUS AND QUANTITATIVE ANALYSIS OF THIOUREA IN COPPER ELECTROLYTE

BACKGROUND OF THE INVENTION

1. Field of the Invention

The present invention relates a continuous flow analytical apparatus for performing precipitation of a target component or impurities, separation of precipitates and analysis of a sample solution in flow injection analysis (referred to as "FI analysis" or "continuous flow analysis" hereinafter) for continuously analyzing the sample solution while flowing it through the capillary. The present invention also relates to a method of determining the amount of thiourea, while precipitating and separating impurities, in a copper electrolyte, on the basis of flow injection analysis (referred to as "FI analysis" or "continuous flow analysis" hereinafter) for continuously analyzing a sample solution while flowing it through a capillary.

2. Discussion of the Background

FI analysis is known in which a sample solution flowing through a capillary is introduced into an analytical portion after a reagent is added to the sample solution, to analyze a target component. An example is a method of measuring impurity concentrations in an electrolyte on the basis of FI analysis in which a buffer is added to a zinc electrolyte as a sample solution flowing through a capillary, reagents which are colored by Co ions and Cu ions in the solution are added to the solution, the sample solution is then introduced into a spectroscopic analyzer for measuring the absorbance of the solution, and the Co ion concentration and Cu ion concentration are determined from the absorbance (Japanese Patent Laid-Open No. 4-32764).

FI analysis has the advantages that a relatively small amount of sample can be precisely analyzed, and that addition of reagents and analysis can be carried out continuously, while flowing a sample solution through a capillary. Therefore, FI analysis is used in various fields. On the other hand, FI analysis requires preparation of a sample solution which produces no precipitate and uses reagents which produce no precipitate, as precipitates cause blocking of the capillary, in order to analyze the sample solution while flowing it through a capillary. Therefore, FI analysis is unsuitable for analysis of a sample solution which easily produces precipitates. Furthermore, when analysis must be performed after a target component or impurities are precipitated and separated, preliminary precipitation out of the system is required. In such a case, the advantages of continuous measurement are lost.

A copper electrolyte generally contains thiourea and glue or gelation added for stabilizing the properties of an electrodeposited metal. The state of electrodeposition is significantly affected by the concentration of these additive. Therefore, determination of these additives is important for controlling operation.

Several conventional methods are known for determining thiourea. An example is a method comprising measuring absorbance by using an iodine-starch solution as a color reagent, and determining the amount of thiourea on the basis of the amount of iodine consumed by the thiourea (Bulletin of the Mining Society of Japan/88 1007 ('72-1) pp.40–44). This method has the advantage of high measurement precision, but is labor intensive due to complicated control of the pH, reaction temperature and time. Since the concentration of an additive, such as thiourea, added to a copper electrolyte changes with time according to the pH, solution temperature and reaction time in the pretreatment process, quantitative analysis must be rapidly and precisely carried out under constant conditions. For example, thiourea in a solution immediately decomposes in the presence of copper and sulfuric acid to produce formidine disulfate, making it impossible to precisely and quantitatively measure the concentration.

A quantitative method is known in which this problem is solved by using FI analysis. In this method, a buffer, an iodine solution and a starch solution are added to a sample solution containing a copper electrolyte while flowing the sample solution through a capillary. The solution colored by the iodine-starch reaction is sent to an absorbance meter to determine the amount of thiourea (Japanese Patent Laid-Open No. 7-258879). This method has the advantage that addition of the reagents, coloring reaction and measurement of absorbance are performed continuously during the flow of the sample solution through the capillary, and thus the amount of thiourea can be determined within a short period of time. However, this method has the problem that the metal ions in the copper electrolyte must be removed in advance. Since the copper electrolyte contains trace amounts of reducing metal ions, such as iron, antimony, arsenic, bismuth, selenium, tin, tellurium, lead, etc., these ions react with the iodine, and therefore these metal ions must removed ahead of time in order to carry out the measurement by FI analysis. However, since FI analysis is performed by analyzing a sample solution while flowing it through a capillary, if precipitates are carelessly produced in removal of these metal ions, measurement might be impossible due to blocking of the capillary.

In the above conventional measurement method, ferric or/and lanthanum ions are initially added to the sample solution out of the system, to produce precipitates of metal impurities, and the precipitates are filtered off before the sample solution is used. As a result, the advantage of FI analysis, that continuous analysis can be made within a short period of time, significantly deteriorates.

The present invention solves the above problems of conventional FI analysis.

SUMMARY OF THE INVENTION

An object of the invention is to enable FI analysis of a sample, which easily produces precipitates, by continuously positively producing and separating precipitates in a capillary and enable high-precision analysis by effectively removing impurities in the solution or separating a target component.

Another object of the invention is to enable continuous quantitative analysis within a short time by providing a precipitation portion and a filtration portion which constitute portions of a measurement pipeline in a measurement system, so as to produce and separate precipitates during the flow of the sample solution through the measurement pipeline.

These objects are provided by a continuous flow analytical apparatus comprising a sample addition portion, a reagent addition portion, a precipitant addition portion and a filtration portion, provided between the sample injection portion and the reagent addition portion, and an analytical portion, wherein the portions are in fluid communication coupled by a measurement pipeline or are switchably in fluid communication coupled by the measurement pipeline.

These objects are also provided by a method for analyzing a sample, comprising adding a precipitant to a sample in a flowing carrier solution in a measurement pipeline; filtering any precipitate from the sample in the measurement pipeline, to form a filtrate; and analyzing the filtrate in the measurement pipeline.

These objects are also provided by a method of determining the amount of thiourea in a copper electrolyte comprising:

a continuous flow analytical method of determining the amount of thiourea in a copper electrolyte comprises adding an iodine-starch solution to the sample solution used as a sample solution to color the copper electrolyte by adding while flowing the sample solution through a measurement pipeline, and determining the amount of thiourea by measuring the absorbance of the solution, wherein a precipitant is added to the sample solution which flows through the measurement pipeline to precipitate impurities, the sample solution containing the precipitates is introduced into the filtrate portion formed in the measurement pipeline to filter and separate the precipitates, a buffer is added to the filtrate to adjust the properties of the solution, and the iodine starch solution is added to color (violet) the solution. This color is discolored in the presence of thiourea, and the degree of discoloration (a change in absorbance) is proportional to the concentration of thiourea, thereby permitting determination of the amount of thiourea.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE INVENTION

Figure 1:
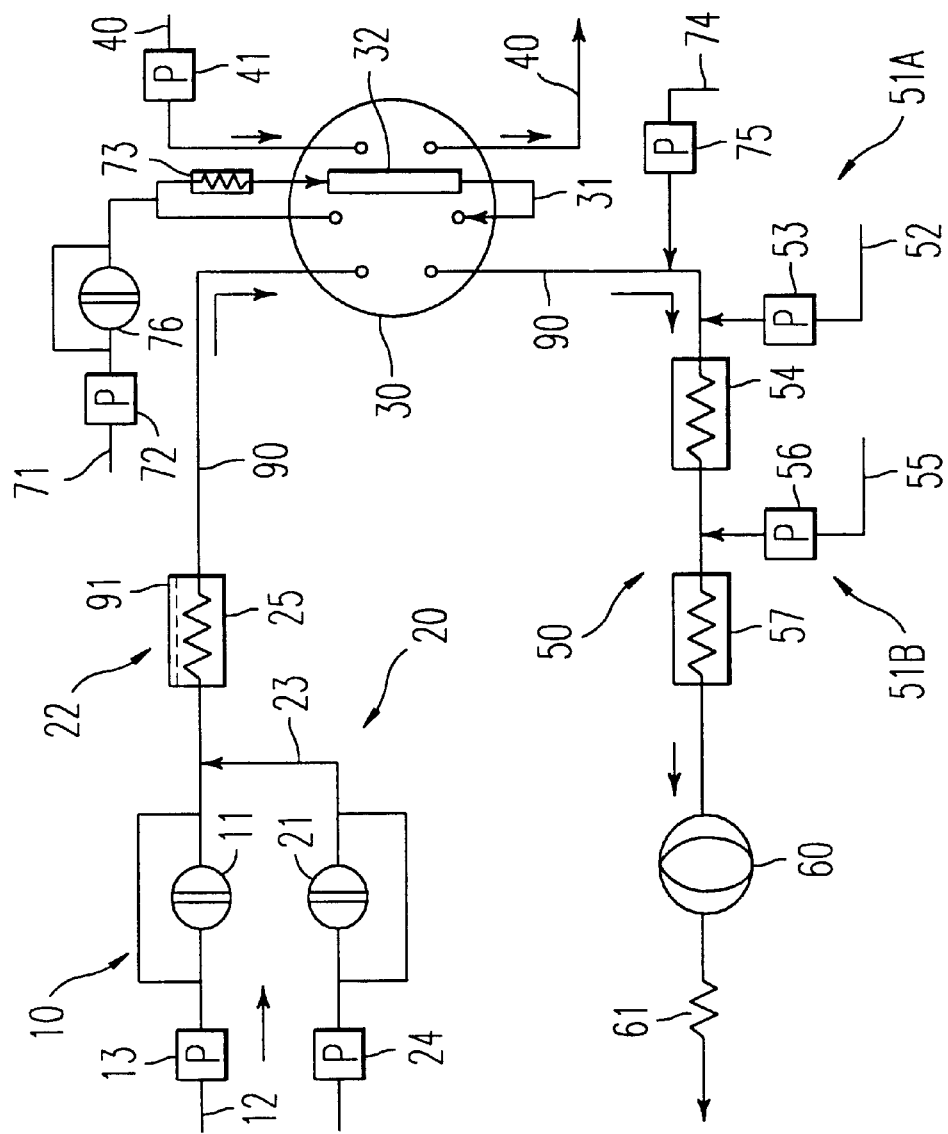
FIG. 1 is a conceptual drawing of a measurement system, i.e., an analytical apparatus, in accordance with the present invention.

FIG. 1 shows an example of the construction of a continuous flow analytical apparatus in accordance with the present invention. The analytical apparatus shown in FIG. 1 comprises a sample injection portion 10, a precipitant addition portion 20, a filtration portion 30, a reagent addition portion 50 and an analytical portion 60, which are integrally connected in order, by a measurement pipeline 90 (referred to as a "pipeline" hereafter) to form a measurement system.

As shown in FIG. 1, the analytical apparatus of the present invention is a continuous flow analytical apparatus in which the sample injection portion 10, the reagent addition portion 50 and the sample analytical portion 60 are integrally connected by the pipeline 90 to form the measurement system so that reaction of the sample and a reagent, and analysis, are continuously made during the flow of the sample through the measurement system by a carrier solution. The analytical apparatus is also a precipitation separation type continuous flow analytical apparatus, in which the precipitant addition portion 20 and the filtration portion 30 are provided between the sample injection portion 10 and the reagent addition portion 50 so that addition of the precipitant, precipitation and filtration, are continuously performed during the flow of the sample solution through the pipeline 90.

The treatment portions 10 to 60 in the measurement system will be described in turn in the direction of flow, as illustrated in FIG. 1.

(A) Sample Injection Portion

The sample injection portion 10 comprises an injection valve 11 for introducing a sample into the pipeline 90, a pipeline 12 for feeding a carrier solution into the pipeline 90, and a feed pump 13 provided in the pipeline 12. The start end of the pipeline 12 is connected to a supply source (not shown) for the carrier solution. The carrier solution is introduced into the pipeline 90 by the feed pump 13 through the pipeline 12, and flows through portions 10 to 60 in the measurement system.

The injection valve 11 is provided with a sample holding portion for holding a predetermined amount of sample. When the valve 11 is opened, the sample holding portion is communicated with the pipeline 90, the carrier solution flows into the sample holding portion to push the sample into the pipeline 90, and the sample flows through the pipeline 90 together with the carrier solution.

(B) Precipitant Addition Portion

To the sample injection portion 10 is connected the precipitant addition portion 20. The precipitant addition portion 20 comprises an injection valve 21 for introducing a precipitant and a mixing portion 22. The injection valve 21 is connected, through a pipeline 23, to the pipeline 90 which passes through the sample injection portion 10, the start end of the pipeline 23 being connected to a supply source (not shown) for the carrier solution through a feed pump 24. The injection valve 21 holds a predetermined amount of precipitant so that when the valve 21 is opened, the precipitant is sent to the pipeline 90 by the carrier solution.

The precipitant mixing portion 22 is downstream of the connection between the supply pipeline 23 for the precipitant and the pipeline 90. The mixing portion 22 has a coil-shaped pipeline 25 in order to secure the fixing time, and has a heater (91) (not shown) if needed. The pipeline 25 forms a part of the pipeline 90, the outlet end thereof being connected to the filtration portion 30. While flowing through the mixing portion 22, the precipitant sent to the sample solution from the injection valve 21 through the pipeline 23 reacts with a target component or impurities in the sample to produce precipitates. The sample solution to which the precipitant is added is sent to the filtration portion 30 through the mixing portion 22.

(C) Filtration Portion

The filtration portion 30 comprises a pipe material (filtration loop) 31 connected to the pipeline 90 and a filter medium 32 with which the pipe material 31 is filled. Examples of the filter medium 32 include a porous material, a filter membrane, a laminate of a porous material and a filter membrane, and the like. The pore size and the porosity of a porous material, the permeability of a filter membrane or the total length of a filter material, the packing of a pipe material, etc. are appropriately determined according to the diameter of the pipe material, the flow rate and the type of precipitates to be filtered.

To the filtration loop 31 of the filtration portion 30 are preferably connected a pipeline 71 for adjusting the properties of the solution, and an injection valve 76 in order to efficiently produce precipitates after the sample solution is introduced into the filtration portion 30, as shown in FIG. 1. The pipeline 71 is connected to the inlet side of the filtration loop 31, and a reaction coil portion 73 is provided between the filtration loop 31 and the connection between the pipeline 71 and the filtration loop 31. A feed pump 72 is provided in the pipeline 71, and the start end of the pipeline 71 is connected to a supply source for a precipitate forming agent or a carrier solution (not shown) for feeding the precipitate forming agent. A solution adjuster, such as ammonia water, for adjusting the properties of the sample solution, is supplied to the filtration portion 30 through the pipeline 71. It is preferable to use the injection valve 76 and hold a predetermined amount of solution adjust or therein. By opening the valve 76, the solution adjustor is pushed out by the carrier solution, and supplied to the filtration portion 30. The sample solution to which the precipitant is added is adjusted by ammonia water or the like when passing through the reaction coil portion 73 of the filtration portion 30 to produce precipitates, and then introduced into the filtration loop 31.

More preferably, the filtration portion is provided with a washing pipeline 40 so that connection of the filtration portion 30 can be switched to the washing pipeline 40 or the pipeline 90. The start end of the washing pipeline 40 is connected to a supply portion (not shown) for a washing solution through a feed pump 41, and the finish end thereof is led to the outside of the system or the next treatment process.

Figure 2:
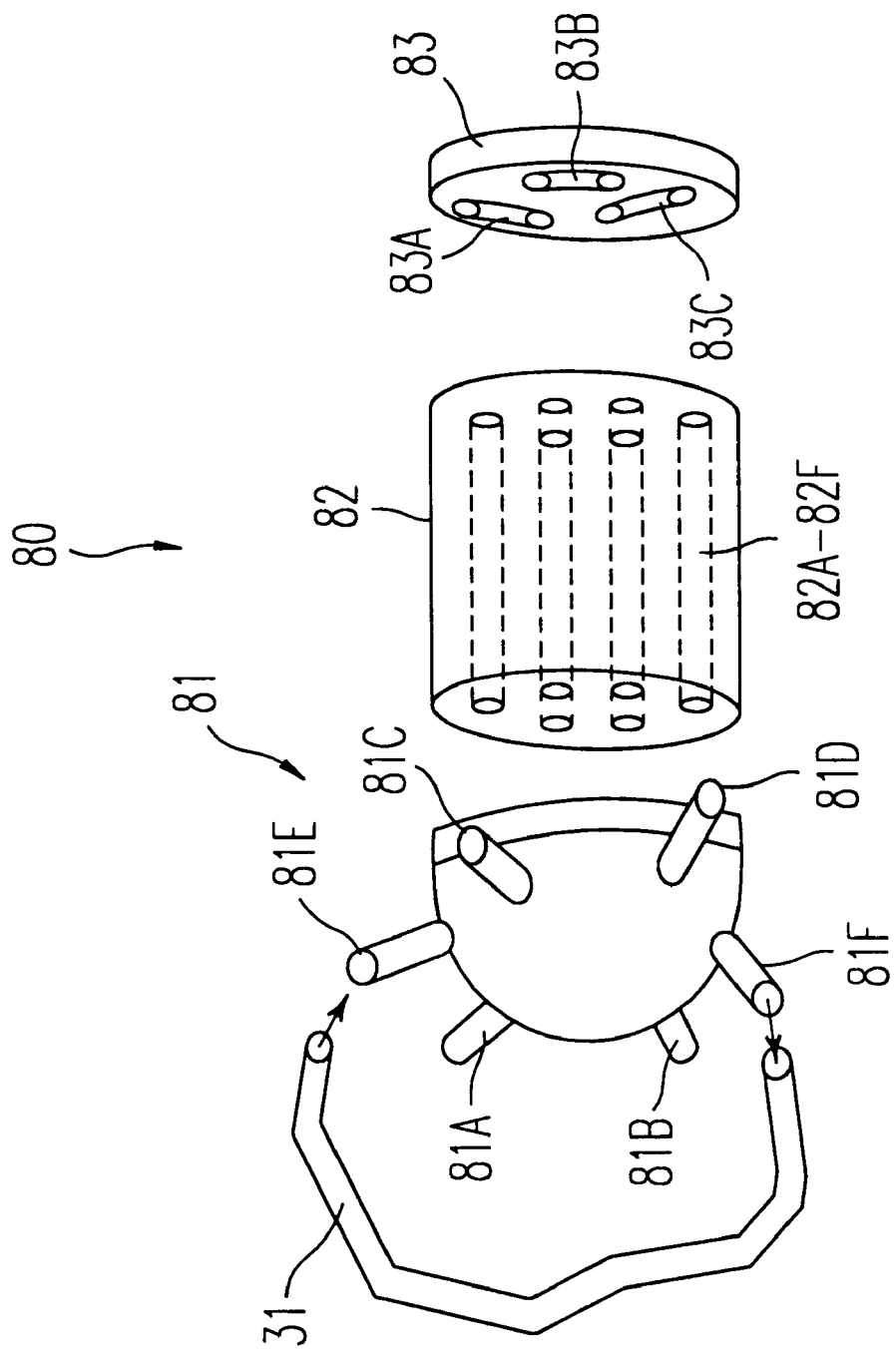
FIG. 2 is a schematic exploded perspective view of a switching valve of a filtration portion.

FIG. 2 shows an example where the filtration portion 30 and the washing pipeline 40 are integrally formed. The construction example comprises a six-way switching valve 80. The switching valve 80 comprises a body 82, and a valve head 81 and a rotating part 83 both of which are provided on both ends of the body 82. On the valve head 81 are provided an inlet port 81a and an outlet port 81b which are connected to the pipeline 90, an inlet port 81c and an outlet port 81d which are connected to the washing pipeline 40, and an inlet port 81e and an outlet port 81f which are connected to the filtration loop (pipe material) 31 filled with the filter medium 32. The filtration loop 31 is provided to connect the inlet port 81e and the outlet port 81f. In the body 82 are provided flow paths 82a to 82f corresponding to the inlet ports 81a, 81c and 81e, and the outlet ports 81b, 81d and 81f, these paths being disposed along the periphery of the body 82.

Figure 3A:
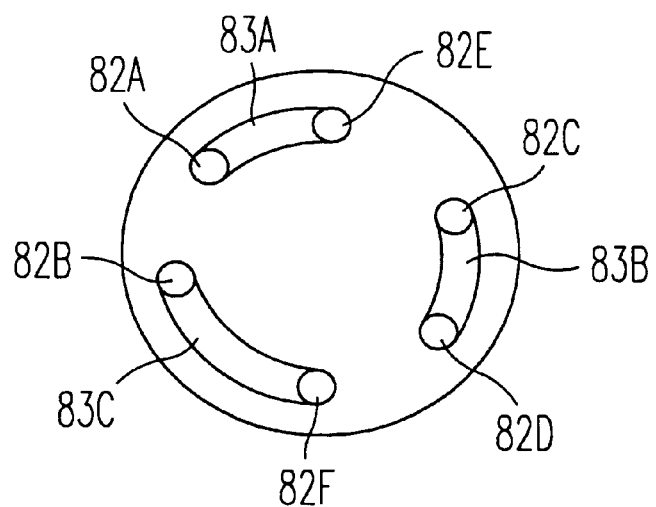
FIGS. 3(a) and (b) are drawings illustrating the connection states of pipelines of the switching valve.

The rotating part 83 is rotatable provided on the body 82. In the rotating part 83 are provided groove 83a, 83b and 83c which respectively connects adjacent paths formed in the body 82. Specifically, as shown in FIG. 3(a), the adjacent flow paths 82a and 82e are communicated with each other by the groove 83a, and similarly the flow paths 82c and 82d, and the flow paths 82f and 82b are communicated with each other by the grooves 83b and 83c, respectively. The positions of the grooves 83a to 83c are moved by rotating (through 60° in the example shown in the drawing) the rotating part 83 to switch the paths.

Figure 3B:
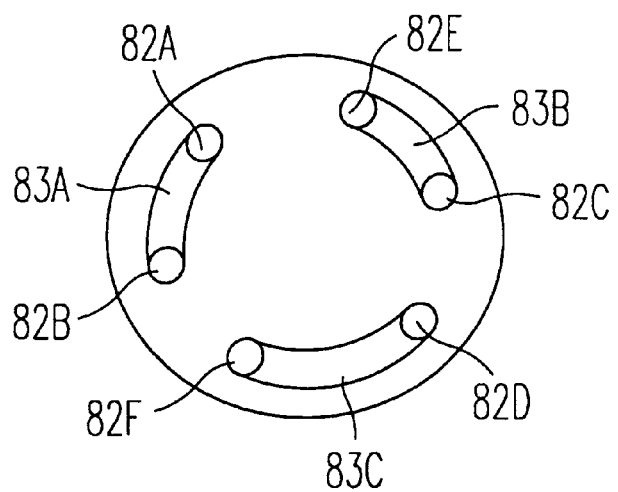

As a result, communication between the flow paths 82a and 82e is cut off, and the flow paths 82a and 82b are communicated with each other, as shown in FIG. 3(b). Similarly, communication between the flow paths 82c and 82d and between the flow paths 82f and 82b is cut off, and the flow paths 82e and 82c and the flow paths 82d and 82f are communicated with each other.

When the switching valve 80 assumes the state shown in FIG. 3(a), the pipeline 90 is connected to the filtration loop 31, the sample solution flows through the filtration loop 31 from the pipeline 90 and again flows through the pipeline 90. The precipitates in the solution are captured by the filter medium 32 and separated from the solution during the flow of the solution through the filtration loop 31, and the filtrate is introduced into the reagent addition portion 50. On the other hand, the washing pipeline 40 is cut off from the pipeline 90. When the paths are switched to the state shown in FIG. 3(b) by the rotating the rotating part 83, connection between the pipeline 90 and the filtration loop 31 is cut off, the filtration loop 31 is connected to the washing pipeline 40, as shown in FIG. 4(b). In this case, the sample solution does not flow through the pipeline 90, and the filtration loop 31 is washed with the washing solution or an elutant to remove the precipitates. After the target component of the sample is precipitated and separated from other impurities, the precipitates dissolved by washing are led to the next treatment step through the pipeline 40.

A solution adjusting pipeline 74 for adjusting the properties of the sample solution is connected between the filtration portion 30 and the reagent addition portion, as needed. The pipeline 74 is connected to the pipeline 90, and a feeding pump 75 is provided in the pipeline 74. An alkaline or acidic solution adjustor or buffer is introduced into the sample solution in the pipeline 90 through the pipeline 74. For example, in determination of the amount of thiourea in a copper electrolyte, the alkaline sample solution (pH 8 to 9) is acidified (pH 4) by adding a hydrochloric acid-sodium acetate mixture to the solution to adjust the solution so that it is suitable for iodine starch reaction.

(D) Reagent Addition Portion

The reagent addition portion 50 comprises a supply portion 51a and a reaction coil portion 54. The supply portion 51a comprises a pipeline for feeding a reagent to the pipeline 90, and a feeding pump provided in this pipeline, the start end of the pipeline being connected to a supply source (not shown) for the reagent. The reaction coil portion 54 comprises a coil-shaped pipeline so that the target component in the sample solution reacts with the reagent to create a state suitable for analysis during the flow of the sample solution through the reaction coil portion 54. For example, a coloring reagent or the like introduced reacts with metal ions of the target component or impurity ions to develop a color with a density corresponding to its concentration.

A plurality of reagent supply portions and pipelines are provided, as needed. For example, in determination of the amount of thiourea in a copper electrolyte, a pipeline 52 for supplying a potassium iodide solution as a reagent and a pipeline 55 for supplying a starch solution are provided. The potassium iodide solution and the starch solution are introduced into the sample solution in the pipeline 90 by feed pumps 53 and 56 provided in the pipelines 52 and 55, through the pipelines 52 and 55, respectively. A reduction decoloring reaction of iodine and thiourea contained in the sample solution proceeds during the flow of the sample solution through the reaction coil portions 54 and 57 provided on the pipeline 90, and residual iodine reacts with the starch to develop color the two reagent supply portions 51a and 51b, comprise pipeline 52 and feed pump 53, and pipeline 55 and feed pump 56, respectively.

(E) Analytical Portion

The analytical portion 60 is provided downstream of the reagent addition portion 50. The analytical portion 60 comprises means, such as a spectrophotometer, for analyzing the target component in the sample solution. The sample solution which reacts with the coloring reagent can be examined to determine the concentration of the target component by the spectrophotometer or the like in the analytical portion 60.

A back pressure adjusting portion 61 for the pipeline 90 is preferably provided in the downstream of the analytical portion 60. The back pressure adjusting portion 61 can be provided by coiling a part of the pipeline 90.

The method of the present invention for determining the amount of thiourea in a copper electrolyte will be described in detail below.

In continuous flow analysis using the continuous flow analytical apparatus of the present invention, the method of determining the amount of thiourea in a copper electrolyte in accordance with the present invention comprises: adding the precipitant to the sample solution which flows through the measurement pipeline to precipitate impurities, leading the sample solution containing precipitates to the filtration portion formed in the measurement pipeline to filter and separate the precipitates, adding the buffer to the filtrate to adjust the solution, adding the iodine-starch solution to develop color, and then determining the amount of thiourea by measuring the absorbance of the solution. In the continuous flow analysis in which the amount of thiourea is determined by adding a iodine-starch solution to the copper electrolytic sample solution to form color, and measuring a change in the absorbance thereof (the degree of discoloration), which is proportionate to the amount of thiourea, while flowing the copper electrolytic sample solution through the measurement pipeline, the method of determining the amount of thiourea in the copper electrolyte comprises adding the precipitant to the sample solution which flows through the measurement pipeline to precipitate impurities, leading the sample solution containing the precipitates to the filtration portion formed in the measurement pipeline to filter and separate the precipitates, adding the buffer to the filtrate to adjust it, and adding the iodine-starch solution to color the solution. This color is discolored in the presence of thiourea, and the degree of discoloration (a change in absorbance) is proportional to the concentration of thiourea, thereby permitting determination of the amount of thiourea.

FIG. 1 shows an example of the measurement system for the determination method of the present invention. In the measurement system for the method of the present invention shown in FIG. 1, the sample injection portion 10, the precipitant addition portion 20, the filtration portion 30, the reagent addition portion 50 and the analytical portion 60 are communicated in turn by the capillary (pipeline) 90. Impurities in the copper electrolyte (copper sulfate solution) as the sample solution are precipitated and separated during the flow of the solution through the measurement system by the carrier solution, and the filtrate is sent to the reagent reaction portion where reaction of the sample and the reagent and analysis are continuously carried out.

In FIG. 1, the pipelines 12, 23, 40, 52, 55, 71 and 74 are connected to the (measurement) pipeline 90, the feed pumps 13, 24, 41, 53, 56, 72 and 75 are respectively provided in these pipelines, and the coil-shaped reaction portions 25, 54, 57 and 73 are formed in the pipeline 90.

The copper electrolyte as the sample solution is held in the injection valve 11 of the sample injection portion 10. By opening the valve 11, the carrier solution flows into the injection valve 11 to push the copper electrolytic sample solution into the pipeline 90, and the copper electrolytic sample solution flows through the pipeline 90 together with the carrier solution to the precipitant addition portion 20 where the precipitant is added to the solution.

The precipitant is held by the injection valve 21 of the precipitant addition portion 20. By opening the valve 21, the carrier solution flows into the valve 21 to push out the precipitant, and the precipitant is added to the copper electrolytic sample solution through the pipeline 23. As the precipitant, ferric ammonium sulfate or lanthanum nitrate is used independently, or an appropriate mixture thereof is used.

The copper electrolytic sample solution to which the precipitant is added is led to the mixing portion 22. The mixing portion 22 comprises the coil-shaped pipeline 25 in order to secure the reaction time, and, if required, has a heater. The copper electrolytic sample solution and the precipitant sufficiently react during the passage of the sample solution through the mixing portion 22.

If precipitates are produced during the flow of the copper electrolytic sample solution toward the filtration portion 30, there is the possibility that the precipitates adhere to the connection portion of the pipeline and the valve. Therefore, after the copper electrolytic sample solution is introduced into the filtration portion 30, the precipitates are preferably produced by adjusting the copper electrolytic sample solution.

Specifically, the pipeline 71 for adjusting the solution is provided on the inlet side of the filtration loop 31 of the filtration portion 30 so that ammonia water or an ammonia solution of ammonium nitrate is supplied to the copper electrolytic sample solution through the pipeline 71 to adjust the sample solution to a pH of 8 to 9. Preferably, the solution adjustor is held by the injection valve 76 provided in the pipeline 71. By opening the valve 76, the carrier solution flows to push out the solution adjustor, and the solution adjustor is supplied to the copper electrolytic sample solution. The copper in the sample solution within this pH region forms a cupro-ammonium complex which dissolves in the solution. on the other hand, arsenic, bismuth, antimony, lead, tin, tellurium and selenium contained in the solution are efficiently coprecipitated together with iron hydroxide or lanthanum hydroxide.

The filtration loop 31 is formed by filling the pipe material, which forms a part of the pipeline 90, with the filter medium 32. Preferably, the washing pipeline 40 is provided on the filtration loop 31 so that the flow path of the filtration portion 30 can be switched to the pipeline 90 or the washing pipeline 40. The filter medium has a pore size of 5 $\mu$m or less, preferably 4 $\mu$m or less. As the filter medium, a porous material having the above pore size, a filter membrane or a laminate thereof is preferably used.

FIG. 2 shows an example of the construction of the filtration portion 30 which uses a six-way switching valve. The six-way valve 80 comprises the valve head 81 having the six holes 81*a* to 81*f*, a pair of the opposite pores 81*e* and 81*f* being connected by the pipe material 31. The pipe material 31 is filled with the filter medium 32 to form the filtration loop. The pores 81*a* and 81*b* are connected to the measurement pipeline 90, and the pores 81*c* and 81*d* are connected to the washing pipeline 40.

On the other hand, in the body 82 are formed the through holes 82*a* to 82*f* which are communicated with the ports 81*a* to 81*f*, respectively, of the head 81, and the rotatable switching portion 83 is provided on the side end of the body 82. In the switching portion 83 are provided the grooves 83*a* to 83*c* for respectively communicating the adjacent two through holes of the through holes 82*a* to 82*f* of the body 82, and the switching portion 83 is rotated (for 60° in the example shown in the drawing) to switch connection between the two through holes of the through holes 82a to 82f to the state shown in FIG. 4(a) or (b).

Figure 4A:
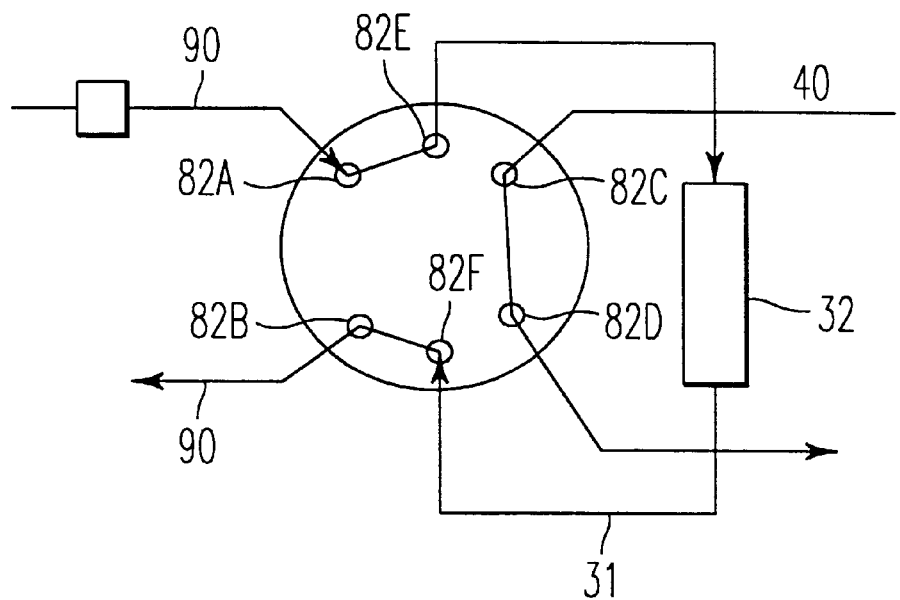
FIGS. 4(a) and (b) are drawings illustrating the connection states of the pipelines of the measurement system corresponding to FIGS. 3(a) and (b), respectively.
Figure 4B:
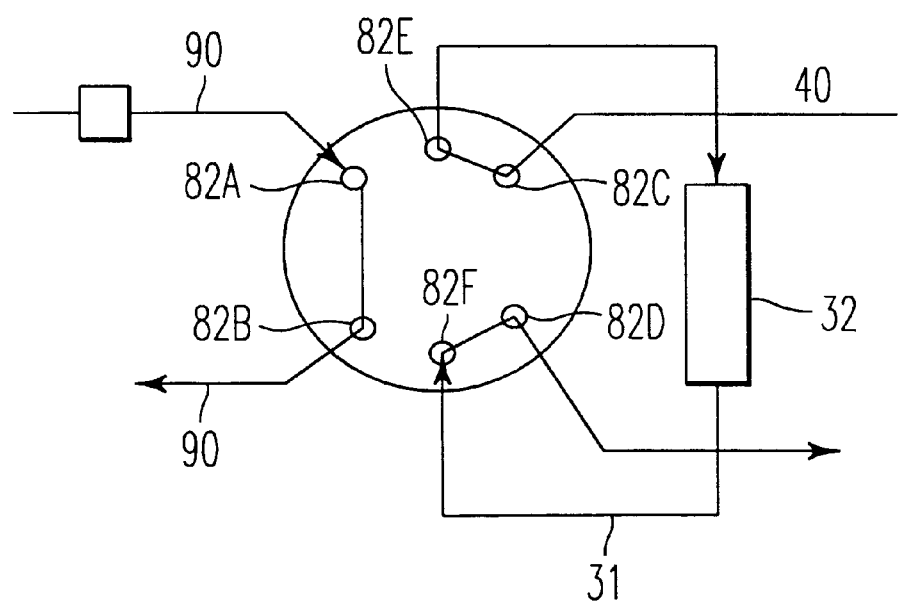

FIG. 4(a) shows the case where the measurement pipeline 90 is connected to the filtration portion 30, and the connection of the washing pipeline 40 is cut off. FIG. 4(b) shows the case wherein each of the through holes 82a to 82f is communicated with the adjacent through hole on the side different from that in the case shown in FIG. 4(a), the filtration portion 30 is connected to the washing pipeline 40, and connection to the measurement pipeline 90 is cut off.

The precipitates in the copper electrolytic sample solution are filtered off during the passage through the filtration portion. The filtrate is sent to the analytical portion, and at the same time, the flow path of the filtration portion 30 is switched to the washing pipeline 40 to remove the precipitates collected by the filter medium by washing.

The buffer (2M HCl.2M NaOAc) is added to the filtrate of the copper electrolytic sample solution passed through the filtration portion 30 to adjust the solution to pH 4, and then the iodine-starch reaction reagent (the iodine-potassium iodide solution and the starch solution) is added to color the solution. The colored solution is led to the absorbance meter to measure the absorbance of the sample solution.

Before measurement of the absorbance of the sample solution, a blank test is carried out before hand for measuring the reference absorbance of the measurement system. Specifically, in a state where the sample solution has not been introduced, the buffer, the solution adjustor, the potassium iodide solution and the starch solution are added to the carrier solution (water), and the absorbance of the resultant solution is measured. The reaction amount of iodine is determined from the difference between the absorbance of the sample solution and the reference absorbance. Since thiourea quantitatively reacts with iodine, the amount of thiourea can be determined from the amount of iodine.

EXAMPLES

Having generally described this invention, a further understanding can be obtained by reference to certain specific examples which are provided herein for purposes of illustration only and are not intended to be limiting unless otherwise specified.

Example 1 and Comparative Example 1 and 2

The amount of thiourea in a copper electrolytic sample solution was determined by using a continuous analytical apparatus having the measurement system shown in FIG. 1 under the measurement conditions shown in Table 1. The results are shown in Table 2.

TABLE 1

| Sample solution | Copper electrolyte 200 μl |
| Carrier Solution | Water 2 ml/min |
| Precipitant | 400 μl of mixture of a ferric sulfate solution (iron content: 15 mg/ml) and a lanthanum nitrate (La content: 5 mg/ml) |
| Precipitant addition portion | pipe diameter 1 mm length 5 m, 100° C. |
| Solution adjustor of the filtration portion | 10% ammonia-0.4 g/ml ammonium nitrate solution 2 ml/min |
| Sample solution in the filtration portion | pH 8–9 |
| Sample solution in the | pH 4 |

TABLE 1-continued

| coloring portion | |
| Coloring reagent | Mixture of potassium iodide and iodine (iodine content: 0.5–5 mg/l) Starch solution (0.01–0.1% concentration) |
| Absorbance meter | U-1000 produced by Hitachi, Ltd. |

TABLE 2

Absorbance and amount of thiourea

| | Example | Comparative Example No. 1 | Comparative Example No. 2 |
| --- | --- | --- | --- |
| Absorbance (Abs) | 0.54 | 0.535 | 0.40 |
| Amount of thiourea ppm | 3.3 | 3.28 | 6.1 |

For the same copper electrolyte as in Example 1, precipitates were previously produced and separated by a manual operation to prepare a sample as a comparative example (No. 1), and the amount of thiourea in the sample was determined by the same method as Example 1. Further, in a comparative example (No. 2), the amount of thiourea in the same copper electrolyte as in Example 1 was determined by using a flow analytical system without the filtration portion for precipitates. The results obtained are also shown in Table 2. In Comparative Example 2, since the precipitates are not separated, measurement error is large, and reliability is low. The results obtained by the method of this example agree with the results obtained by measurement after the precipitates are previously separated, and thus has high reliability.

In Example 1, connection of the filtration portion 30 was switched to the washing pipeline 40 to supply the washing solution (2M-HCl) to the filtration portion 30 through the pipeline 40 and dissolve the precipitates deposited in the filter medium, and the resultant solution was sent to an induction plasma emission spectroscopic analytical apparatus (ICP-AES) connected to the outlet end of the pipeline 40. The concentrations of the impurities recovered as the precipitates were measured by the apparatus, and the rates of recovery of impurities in the copper electrolyte used as the sample were determined. As a result, the rates of recovery of arsenic, antimony and bismuth were 98 to 99%.

A copper electrolyte, to which impurities were added so that the impurity concentrations were 50% or 100% greater than the impurity concentrations of the original copper electrolyte were used as samples. The rates of recovery in the impurities of the sample were measured by the same method as described above using the same apparatus. The results obtained are shown in Table 3. Table 3 indicates that the rates of recovery are substantially constant regardless of the amounts of the impurities added, and that separation of impurities in the copper electrolyte by the apparatus is very reliable. Table 4 shows a comparison between the treatment time up to the end of measurement using the apparatus of the present invention and the treatment time of quantitative measurement by a conventional batch method, the quantitative analysis using the apparatus of the present invention can significantly reduce the treatment time, as compared with the batch method.

TABLE 3

Results of Impurity Test

|    | Adding amount/μl | Recovery/μl | Rate of recovery/% |
|----|------------------|-------------|--------------------|
| As | —                | 20          | —                  |
|    | 10.0             | 29.7        | 99                 |
|    | 20.0             | 39.6        | 99                 |
| Sb | —                | 10          | —                  |
|    | 10.0             | 19.8        | 99                 |
|    | 20.0             | 29.1        | 97                 |
| Sn | —                | 10          | —                  |
|    | 5                | 15.0        | 100                |
|    | 10               | 19.2        | 96                 |
| Bi | —                | 10          | —                  |
|    | 5                | 14.9        | 99                 |
|    | 10               | 19.8        | 99                 |
| Pb | —                | 10          | —                  |
|    | 5                | 14.9        | 100                |
|    | 10               | 19.8        | 99                 |

TABLE 4

Comparison of Treatment Time

|                | Batch method (conventional method) | Analytical apparatus of this invention |
|----------------|------------------------------------|----------------------------------------|
| Treatment time | 240 min                            | 10 min                                 |

Example 3 and Comparative Example 3

A continuous flow analytical apparatus having the measurement system shown in FIG. 1 was used. 200 μl of electrolytic sample solution was put in the sample injection valve 11, water as the carrier solution was introduced at a flow rate of 2 ml/min, and then the valve 11 was opened to introduce the copper electrolyte sample solution into the measurement pipeline 90. Similarly, 400 μl of a mixture of a ferric sulfate solution (iron content: 15 mg/ml) and a lanthanum nitrate solution (La content: 5 mg/ml) as a precipitant was put in the injection valve 21, and the carrier (water) was passed to inject the precipitant into the copper electrolyte sample solution. The copper electrolytic sample solution was led to the reaction portion 25. The reaction portion 25 comprised a portion formed by coiling a pipeline having a diameter of 1 mm and a length of 5 m, and was heated to 100° C. The sample solution and the precipitant were sufficiently mixed during passage through the reaction portion 25, and the sample solution was then led to the filtration portion 30. On the other hand, 600 μl of 10% ammonia-0.4 g/ml ammonium nitrate solution was put in the injection valve 76, and then added to the cooper electrolytic sample solution at a flow rate of 2 ml/min by passing the carrier (water) to adjust the sample solution to a pH of 8 to 9. The sample solution was then led to the filtration loop 31, and the precipitates in the solution were filtered and separated therein.

2HCl.2 M NaOAc was added as the buffer at a flow rate of 2 ml/min to the filtrate led from the filtration portion 30 to acidify (pH 4) the sample solution, and then a mixture of potassium iodide and iodine (iodine content: 0.5 to 5 mg/ℓ) was added at a flow rate of 1 ml/min to the sample solution (filtrate), and the starch solution of 0.01 to 0.1% was further added to color the solution.

The colored sample solution was introduced into an absorbance meter (produced by Hitachi Co. U-1000) to measure the absorbance. The amount of thiourea was determined from the absorbance by using a calibration curve previously obtained. The results are shown in Table 5.

TABLE 5

Absorbance and Amount of Thiourea

|                      | Example | Comparative Example No. 1 | Comparative Example No. 2 |
|----------------------|---------|---------------------------|---------------------------|
| Absorbance (Abs)     | 0.54    | 0.535                     | 0.40                      |
| Amount of thiourea ppm | 3.3   | 3.28                      | 6.1                       |

Figure 5:
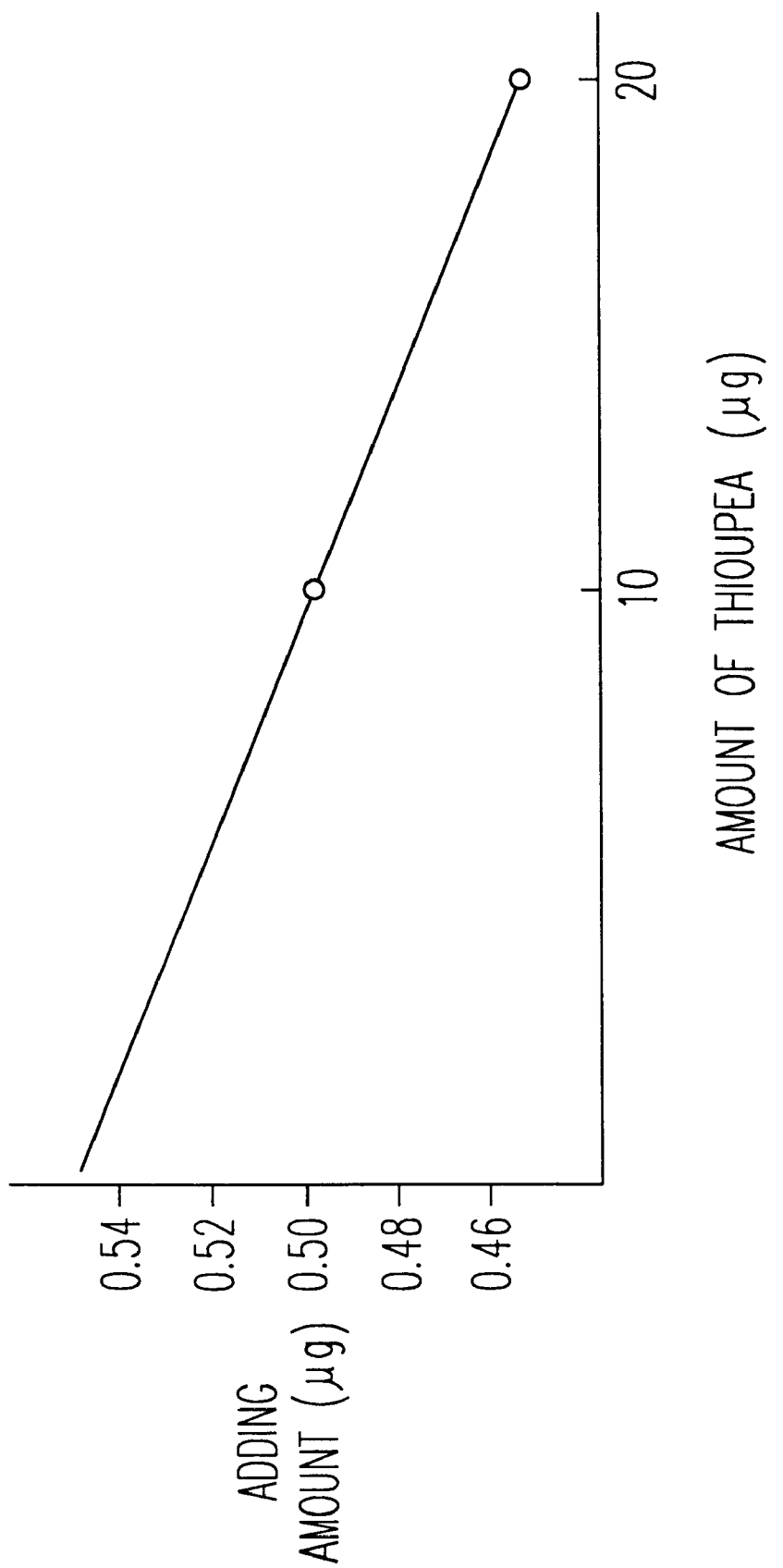
FIG. 5 is a graph showing a calibration curve.

The calibration curve was formed by the same measurement of absorbance as this example using reference solutions which were obtained by sufficiently heating a copper electrolyte to decompose and remove thiourea, cooling the copper electrolyte, and then adding stepwisely predetermined amounts of thiourea reference solution to the copper electrolyte. The thus obtained calibration curve is shown in FIG. 5.

In regard to the various metal impurities contained in the copper electrolyte, the rates of separation of the precipitates separated by the filtration portion 30 are shown in Table 6. The table indicates that almost all impurity metals in the copper electrolytic sample solution are separated as the precipitates from the solution.

TABLE 6

Rates (%) of Presence of Impurity metals

| Impurity metal  | Fe | La | As | Sb | Bi |
|-----------------|----|----|----|----|----|
| Precipitate     | 97 | 99 | 99 | 98 | 99 |
| In the filtrate | 3  | 1  | 1  | 2  | 1  |

A sample solution obtained by previously adding the precipitant to the copper electrolyte to separate the precipitates was used as a comparative sample (Comparison No. 1). 100 ml of the buffer was added to 10 ml of sample solution, and 20 ml and 5 ml of the potassium iodide solution and the starch solution, respectively, were further added to color the solution. The absorbance of the colored solution was measured. The results are shown in Table 5.

With another comparative sample (Comparison No. 2), a conventional flow analytical measurement system without the precipitation portion and the filtration portion shown in the measurement system of FIG. 1 was used, and the absorbance was measured by the same method as Example 3 except production and separation of the precipitates. The amount of thiourea was determined from the absorbance. The results obtained are also shown in Table 5.

The results shown in Table 5 indicate that the results of measurement in this example agree with the results obtained in the case where the precipitates were previously removed. It was thus confirmed that the amount of thiourea can precisely be determined without previous removal of impurities in the sample solution. On the other hand, the conventional flow analysis (Comparison No. 2) has large measurement error and low reliability because the precipitates were not removed.

The continuous flow analytical apparatus of the present invention is capable of continuously separating precipitates and analyzing a target component during passage of a sample solution through the pipeline. Therefore, continuous FI analysis can be carried out for samples which are normally unsuitable for conventional FI analysis, such as a sample which contains large amounts of impurities, and requires precipitation and removal of the impurities, a sample which requires precipitation and separation of a target component for analysis, etc. In addition, since precipitation, separation of precipitates and analysis of a target component are automatically performed during passage through the pipeline, analytical results with high precision and no user error can be obtained.

The priority documents of the present application, Japanese Patent Applications Hei 8-258400 and Hei 8-258401, both filed Sep. 30, 1996, are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A flow analysis apparatus comprising:
    a capillary flow path, said capillary flow path comprising:
    a sample addition portion,
    a precipitant addition portion downstream of said sample addition portion,
    a heated reaction zone downstream of said precipitant addition portion,
    a filtration portion downstream of said heated reaction zone,
    a reagent addition portion downstream of said filtration portion, and
    an analytical portion downstream of said reagent addition portion,
    wherein said filtration portion comprises a washing pipeline and a filtration loop, the filtration loop in fluid communication with a solution adjustor supply pipeline, the filtration portion being capable of selectively connecting the filtration loop in fluid communication with both the heated reaction zone and the reagent addition portion or the washing pipeline.

2. The flow analysis apparatus of claim 1, wherein said filtration portion further comprises a switching valve, said switching valve including said filtration loop.

3. A method of analyzing a copper electrolyte sample with said apparatus of claim 1 comprising:
    adding a precipitant to said sample of copper electrolyte in a flowing carrying solution in said capillary flow path to form a first solution and heating said first solution in said first reaction zone, adding a solution adjustor containing aqueous ammonia, whereby copper forms a solution of cupro-ammonium complex, and whereby a member of the group consisting of arsenic, bismuth, antimony, lead, tin, tellurium and selenium is precipitated together with iron hydroxide or lanthanum hydroxide;
    filtering any precipitate in said capillary flow path with said filtration portion, to form a filtrate;
    adding a buffer to said filtrate;
    adding an iodine-starch reagent to the filtrate in said capillary flow path with said reagent addition portion; and
    analyzing said filtrate for thiourea by measuring absorbance of said filtrate in said capillary flow path with said analytical portion.

4. The method of claim 3, further comprising:
    after adding said reagent to the filtrate, connecting said filtration loop into fluid communication with said washing pipeline; and
    washing said filtration loop with a washing solution.

5. The method of claim 3, further comprising:
    after said analyzing the filtrate, connecting said filtration loop into fluid communication with said washing pipeline; and
    washing said filtration loop with a washing solution.

6. The method of claim 3, wherein said precipitant comprises ferric ammonium sulfate and/or lanthanum nitrate; and wherein said filtration loop comprises a filter medium having a pore size at most 5 $\mu$m.

7. The method of claim 3, wherein said filtration portion further comprises a switching valve, said switching valve including said filtration loop and said method further comprises, after adding said iodine-starch reagent, switching fluid communication of said filtration loop to said washing pipeline; and
    washing said filtration loop with a washing solution.

8. The method of claim 3, wherein said adding said iodine-starch reagent to said filtrate comprises adding a starch solution to said filtrate, and adding an iodine solution to said filtrate.

* * * * *